United States Patent
Vu et al.

(10) Patent No.: US 6,911,195 B2
(45) Date of Patent: Jun. 28, 2005

(54) GEL ANTIPERSPIRANT COMPOSITION CONTAINING VOLATILE LINEAR SILICONE AND CALCIUM ENHANCED ANTIPERSPIRANT SALT

(75) Inventors: Tuan M. Vu, Canton, MA (US); Yan-Fei Shen, Canton, MA (US)

(73) Assignee: The Gillette Company, Boston, MA (US)

( * ) Notice: Subject to any disclaimer, the term of this patent is extended or adjusted under 35 U.S.C. 154(b) by 260 days.

(21) Appl. No.: 10/320,202

(22) Filed: Dec. 16, 2002

(65) Prior Publication Data

US 2004/0115147 A1 Jun. 17, 2004

(51) Int. Cl.[7] ............................. A61K 7/32; A61K 7/34; A61K 7/38; A61K 7/00
(52) U.S. Cl. ............................. 424/65; 424/66; 424/68; 424/400; 424/401
(58) Field of Search .............................. 424/65, 66, 68, 424/400, 401

(56) References Cited

U.S. PATENT DOCUMENTS

| 5,162,378 A | 11/1992 | Guthauser ................ 424/66 |
| 5,534,246 A | 7/1996 | Herb et al. ................ 424/66 |
| 5,587,153 A | 12/1996 | Angelone, Jr. et al. ....... 424/66 |
| 5,925,338 A | 7/1999 | Karassik et al. ............. 424/65 |
| 5,955,065 A | 9/1999 | Thong et al. ............... 424/68 |
| 6,042,816 A | 3/2000 | Shen ....................... 424/65 |
| 6,245,325 B1 | 6/2001 | Shen ....................... 424/65 |

FOREIGN PATENT DOCUMENTS

| WO | WO 91/08732 | 6/1991 |
| WO | WO 02/26204 | 4/2002 |
| WO | WO 2004/012694 | 2/2004 |

OTHER PUBLICATIONS

Copy of International Search Report in PCT/US 03/39813.

Primary Examiner—Shelley A. Dodson
(74) Attorney, Agent, or Firm—Stephan P. Williams

(57) ABSTRACT

Disclosed are antiperspirant compositions, particularly clear gel antiperspirant compositions, that are water-in-silicone oil emulsions. The emulsion includes a water phase, typically comprising about 65% to about 95% by weight of the emulsion, and a silicone oil phase, typically comprising about 5% to about 35% by weight of the emulsion. The water phase includes an antiperspirant salt dissolved therein, typically in an amount of about 8% to about 30% by weight of the emulsion, the antiperspirant salt comprising a calcium enhanced aluminum-zirconium chlorohydrate. The silicone oil phase contains less than about 5% by weight of the emulsion of a non-volatile oil and includes about 2% to about 25% by weight of the emulsion of a volatile linear silicone.

18 Claims, No Drawings

GEL ANTIPERSPIRANT COMPOSITION CONTAINING VOLATILE LINEAR SILICONE AND CALCIUM ENHANCED ANTIPERSPIRANT SALT

BACKGROUND OF THE INVENTION

The present invention relates to antiperspirant compositions that are water-in-oil emulsions, particularly clear gel compositions.

In U.S. Pat. No. 5,587,153 there is described clear gel antiperspirant compositions which are water-in-oil emulsions. The water phase includes a solubilized antiperspirant salt and the oil phase includes a silicone oil. Clarity is obtained by matching the refractive index of the two phases. These clear gel compositions cannot use conventional enhanced efficacy antiperspirant salts because such salts are unstable in aqueous solution and revert to non-enhanced form. Thus, the clear gel antiperspirant compositions do not achieve the highest possible antiperspirant efficacy. Nonetheless, the clear gel antiperspirant compositions marketed in the early 1990's achieved extraordinary commercial success.

In U.S. Pat. No. 5,925,338 there is described clear gel antiperspirant compositions with reduced fabric staining. These compositions are essentially identical to those described in the aforementioned '153 patent except that the non-volatile silicone oil has been reduced below about 5% and the compositions include a volatile linear silicone.

In U.S. Pat. No. 6,245,325 there is described enhanced efficacy antiperspirant salts which are stable in aqueous solution. These salts include a soluble calcium salt such as calcium chloride and a soluble amino acid such as glycine. Typically, these salts have a Ca:Al+Zr weight ratio of about 1:1 to about 1:28 and an amino acid:Al+Zr weight ratio of about 2:1 to about 1:20. Because these salts retain their enhanced efficacy in aqueous solution, they have an advantage over conventional enhanced efficacy salts which revert to the non-enhanced form in aqueous solution. For the sake of brevity, these salts are hereinafter identified as "CEAZCH" for calcium enhanced aluminum-zirconium chlorohydrate.

It had been hoped that the CEAZCH salts could be used to replace the conventional salts currently employed in the commercially marketed clear gel antiperspirant products in order to improve the antiperspirant efficacy of those products. Thus, in example 8 of the aforementioned '325 patent there is disclosed a clear gel antiperspirant composition containing CEAZCH. While this product had a higher efficacy than the commercially sold gel, the improvement in efficacy was not as high as desired. Moreover, the product had unacceptable application aesthetics, namely it produced unacceptable whitening and/or white clumps on the skin and hair. When it was attempted to reduce the whitening by addition of non-volatile emollient, this reduced the efficacy and exacerbated the formation of white clumps, rendering the product unacceptable.

It would be highly desirable to produce an emulsion antiperspirant composition, particularly a clear gel antiperspirant composition, with significantly improved antiperspirant efficacy over commercially available antiperspirant gel products. It would be particularly desirable to produce such a product that eliminated any undesirable application aesthetics, such as formation of white clumps on the skin and hair.

SUMMARY OF THE INVENTION

The present invention embraces an antiperspirant composition, particularly a clear gel antiperspirant composition, that is a water-in-silicone oil emulsion. The emulsion includes a water phase, typically comprising about 65% to about 95% by weight of the emulsion, and a silicone oil phase, typically comprising about 5% to about 35% by weight of the emulsion. The water phase includes an antiperspirant salt dissolved therein, typically in an amount of about 8% to about 30% by weight of the emulsion, the antiperspirant salt comprising a calcium enhanced aluminum-zirconium chlorohydrate. The silicone oil phase contains less than about 5% by weight of the emulsion of a non-volatile oil and includes about 2% to about 25% by weight of the emulsion of a volatile linear silicone. Clarity may be obtained by either matching the refractive index of the two phases (see, for example, U.S. Pat. No. 5,587,153) or by formulating the product as a microemulsion (see, for example, WO 02/26204). If a gel is desired, the viscosity of the gel may be increased or decreased by changing the proportion of oil to water and/or by subjecting the composition to more or less high shear mixing.

DETAILED DESCRIPTION OF THE INVENTION

The antiperspirant compositions of the present invention are water-in-silicone oil emulsions. The water phase comprises about 65% to about 95%, preferably about 70% to about 90%, by weight of the emulsion. The silicone oil phase comprises about 5% to about 35%, preferably about 10% to about 30%, by weight of the emulsion. The water phase includes about 8% to about 30%, preferably about 10% to about 28%, by weight of the emulsion of an antiperspirant salt dissolved therein, the antiperspirant salt comprising a calcium enhanced aluminum-zirconium chlorohydrate. The amount of antiperspirant salt should be that amount which provides the composition with about 5% to about 22% USP active, preferably about 10% to about 20% USP active. The silicone oil phase contains less than about 5%, preferably 0% to about 3%, by weight of the emulsion of a non-volatile silicone. The silicone oil phase includes about 2% to about 25%, preferably about 5% to about 15%, by weight of the emulsion of a volatile linear silicone.

The antiperspirant salts which may be utilized in the compositions of the present invention are calcium enhanced aluminum-zirconium chlorohydrate (CEAZCH) salts. By this is meant antiperspirant salts as described in U.S. Pat. No. 6,245,325, which is incorporated herein by reference. These salts are aluminum-zirconium chlorohydrates (Al:Zr= 2–10; M:Cl=0.9–2.1) that, as 10% solutions, have an HPLC peak 4 to peak 3 area ratio of at least 0.5, preferably at least 0.7, with at least 70%, preferably at least 80%, of the aluminum contained in said peaks 3 and 4. These salts include a soluble calcium salt in an amount to provide a Ca:Al+Zr weight ratio of about 1:1 to about 1:28, preferably about 1:2 to about 1:25. They also include a water soluble amino and/or hydroxy acid in an amount to provide an acid:Al+Zr weight ratio of about 2:1 to about 1:20, preferably about 1:1 to about 1:10. Typical calcium salts include calcium chloride, calcium bromide, calcium nitrate, calcium citrate, calcium formate, calcium acetate, calcium gluconate, calcium ascorbate, calcium lactate, calcium glycinate and mixtures thereof. Typical amino and/or hydroxy substituted lower alkanoic acids include any of the amino acids such as glycine, alanine, valine, leucine, isoleucine, β-alanine, serine, cysteine, β-amino-n-butyric acid, γ-amino-n-butyric acid, etc. and hydroxy acids such as glycolic acid and lactic acid.

The silicone oil phase typically includes a volatile cyclic silicone and a silicone copolyol (or polyether) surfactant to emulsify the water phase into the silicone phase. The silicone copolyol surfactant is typically a polyethylene glycol/polypropylene glycol modified polyorganosiloxane with an HLB of about 4 to about 12. The volatile cyclic silicone and silicone copolyol surfactant may be added as separate components, for example, decamethylcyclopentasiloxane (D5) and dimethicone copolyol (DC 190 or DC 193), respectively. In such a case, the silicone copolyol surfactant is typically present in an amount of about 0.3% to about 3%, more typically about 0.5% to about 1.5%, by weight of the emulsion. The volatile cyclic silicone and silicone copolyol surfactant are also conveniently available as a mixture and may be used as such. For example, Dow Corning 3225C and Dow Corning 5225C are mixtures comprising 90% volatile cyclic silicone (D4 and D5, respectively) and 10% silicone copolyol (PEG/PPG-18/18 dimethicone). Similar silicone copolyol mixtures are available from other manufacturers such as, for example, Goldschmidt (Abil EM97), Shin Etsu (KSG 21), and General Electric.

The silicone oil phase should contain less than about 5%, preferably 0% to about 3%, most preferably 0% to about 2%, by weight of the emulsion of a non-volatile oil. Non-volatile oils include non-volatile silicones and other organic emollient oils. By non-volatile is meant a liquid oil that does not have a significant vapor pressure at 25° C. and has flash point greater than 100° C. The non-volatile silicones typically have a viscosity of about 5 to about 1000 cst (5–1000 $mm^2/s$), preferably about 10 to about 500 cst (10–500 $mm^2/sec$), and include, for example, polyalkylsiloxanes such as dimethicone (e.g., DC 200), polyphenylsiloxanes (e.g., DC 710 or DC 555) and polyalkylarylsiloxanes such as phenyltrimethicone (e.g., DC 556). The organic oils include liquid aliphatic hydrocarbons such as mineral oil, hydrogenated polyisobutene, polydecene, paraffins and isoparaffins; liquid aliphatic alcohols such as octyldodecanol and isostearyl alcohol; liquid fatty alcohol esters such as $C_{12-15}$ alkyl benzoate, $C_8$ alkyl benzoate, isostearyl benzoate, octyldodecyl benzoate and myristyl octanoate; liquid fatty acid esters such as isopropyl palmitate, isopropyl myristate, isostearyl isostearate and octyl isononanoate; and liquid dicarboxylic acid esters such as dusopropyl sebacate. It has been found that the presence of non-volatile oil tends to reduce the antiperspirant efficacy of the composition. In addition, it appears to cause the CEAZCH salt to form white clumps on application. However, a small amount of a non-volatile oil, particularly a non-volatile silicone, for example, about 0.5% to about 3%, may be desirable to prevent whitening.

The silicone oil phase includes about 2% to about 25%, preferably about 5% to about 15%, by weight of the emulsion of a volatile linear silicone. By volatile is meant a liquid that has a measurable vapor pressure at 25° C. and a flash point less than 100° C. It has been found that the volatile linear silicone improves the efficacy and application aesthetics of the composition. Suitable volatile linear silicones include those having the formula $(CH_3)_3SiO\{(CH_3)_2SiO\}_xSi(CH_3)_3$, wherein x is 0–7, preferably 0–5. Preferably the volatile linear silicone has a boiling point less than 250° C. and a viscosity of about 0.5–4.0 centistokes ($mm^2/s$), preferably about 0.6–3.0 $mm^2/s$. Examples of representative volatile linear silicones include hexamethyldisiloxane (MM) which has a boiling point of 100° C., a viscosity of 0.65 $mm^2/s$, and formula $Me_3SiOSiMe_3$; octamethyltrisiloxane (MDM) which has a boiling point of 152° C., a viscosity of 1.04 $mm^2/s$, and formula $Me_3SiO(Me_2SiO)SiMe_3$, decamethyltetrasiloxane ($MD_2M$), which has a boiling point of 194° C., a viscosity of 1.53 $mm^2/s$, and formula $Me_3SiO(Me_2SiO)_2SiMe_3$; dodecamethylpentasiloxane ($MD_3M$), which has a boiling point of 229° C., a viscosity of 2.06 $mm^2/s$, and formula $Me_3SiO(Me_2SiO)_3SiMe_3$; tetradecamethylhexasiloxane ($MD_4M$), which has a boiling point of 245° C., a viscosity of 2.63 $mm^2/s$, and formula $Me_3SiO(Me_2SiO)_4SiMe_3$; and hexadecamethylheptasiloxane ($MD_5M$), which has a boiling point of 270° C., a viscosity of 3.24 $mm^2/s$, and formula $Me_3SiO(Me_2SiO)_5SiMe_3$. Preferred volatile linear silicones include DC 200 (1.5 cst) and DC 2-1184 (dimethicone and trisiloxane; 1.7 cst), both available from Dow Corning.

The water phase may also include lower alkanols, such as ethanol, and/or polyhydric alcohols (typically with 3 to 9 carbon atoms), such as propylene glycol, dipropylene glycol, tripropylene glycol or sorbitol. If included in the composition, the total amount of lower alkanol will generally comprise less than 15% of the composition, typically about 3% to about 12%, by weight. The amount of polyhydric alcohol, if included, will fall within the range of about 0.5% to about 10%, preferably about 1% to about 5%, of the composition by weight. The amount of polyhydric alcohol should ideally be kept to a minimum because it is believed to somewhat adversely impact efficacy.

The foregoing list of materials is by way of example only and is not intended to be a comprehensive list of all potential materials that may be useful in an antiperspirant composition. Obviously, the skilled worker may select materials which provide the desired application and aesthetic characteristics of the particular form of antiperspirant composition to be produced. For example, the antiperspirant composition may include a fragrance, an encapsulated fragrance, a colorant, a deodorant active agent, or an odor-masking agent.

The antiperspirant composition may be formulated as a liquid or gel, and is preferably formulated as a gel having a viscosity of about 30,000 cP (30 Pas) to about 300,000 cP (300 Pas), preferably about 50,000 cP (50 Pas) to about 200,000 cP (200 Pas). The latter viscosity range is measured at 21° C. using a Brookfield RV viscometer with a helipath stand and T-C spindle at 5 RPM. Lower viscosities (30–50 Pas) can be measured with a T-B spindle at 5 RPM, and higher viscosities(200–300 Pas) can be measured with a T-D spindle at 5 RPM. The viscosity of the gel may be increased or decreased by changing the proportion of oil to water and/or by subjecting the composition to more or less high shear mixing. The composition may be made clear (e.g., clarity better than 100 NTU, preferably better than 50 NTU, at 21° C.) by either closely matching (e.g., to 0.0005 or better) the refractive index of the two phases (see, for example, U.S. Pat. No. 5,587,153) or by formulating the product as a microemulsion (see, for example, WO 02/26204).

The present invention may be further illustrated by the following examples in which the parts and percentages are by weight.

EXAMPLE

Clear antiperspirant gel compositions comprising the following ingredients, in which all parts and percentages are by weight, were prepared in the following manner. The water phase components (AZCH'-Gly/Ca, propylene glycol, ethanol, water) and the oil phase components are each mixed in separate containers and filtered and the refractive index of each is measured. The refractive index of the water phase is adjusted to match the refractive index of the oil phase to within 0.0004 by addition of water or propylene glycol as required. The water phase is then slowly added to the oil phase at about 18° C. with sufficient mixing to form a clear emulsion with minimum aeration. This emulsion is then sheared to form a clear gel with a viscosity of about 130,000 to 160,000 cP (130–160 Pas).

| | Weight Percent | | | |
|---|---|---|---|---|
| Ingredient | Comp. 1 | Comp. 2 | Ex. 1 | Ex. 2 |
| Water | 5.5 | 4.5 | 14.9 | 8.37 |
| Al—Zr Chlorohydrate-Gly/Ca (27.5%)[1] | 65.5 | 65.4 | 61.8 | |
| Al—Zr Chlorohydrate-Gly/Ca (29%)[2] | | | | 60.63 |
| Propylene Glycol | 1.0 | 2.0 | 3.0 | 2.25 |
| Ethanol | 10.0 | 10.0 | 3.0 | 11.00 |
| Dimethicone (DC 225)[3] | 9.7 | 9.6 | | |
| Dimethicone (DC 200 5 cst)[3] | | | 1.0 | |
| Dimethicone (DC 200 10 cst)[3] | | | | 1.75 |
| Phenyl trimethicone (DC 556)[3] | | 0.1 | | |
| Dimethicone Copolyol (DC-3225C)[4] | 8.1 | 8.1 | 7.7 | |
| Dimethicone Copolyol (DC-5225C)[4] | | | | 9.60 |
| Dimethicone (1.5 cst DC 200)[5] | | | 8.3 | |
| Dimethicone & Trisiloxane[5] (1.7 cst DC 2-1184) | | | | 6.15 |
| Fragrance | 0.2 | 0.3 | 0.3 | 0.25 |

[1]Aqueous solution containing 27.5% USP active (Al:Zr = 3.6; M:Cl = 1.4; peak 4:3 > 1), 4% glycine and 1.8% Ca. Final gel composition contains ~18% USP active (Comp. 1&2) and ~17% USP active (Ex. 1).
[2]Aqueous solution containing 29% USP active (Al:Zr = 5.2; M:Cl = 1.16; peak 4:3 > 1), 3.3% glycine and 1.8% Ca. Final gel composition contains ~18% USP active (Ex. 2).
[3]Non-volatile silicone
[4]Silicone polyether surfactant (10%) in cyclomethicone
[5]Volatile linear silicone The products of the above examples were compared to Gillette® Series Clear Gel Antiperspirant, which has a similar formulation to Comp.1, but contains non-enhanced aluminum-zirconium tetrachlorohydrate-gly, the only previously available aqueous form. The products were tested for thermal efficacy (i.e., hot room sweat reduction) on female panelists in separate panel studies (AvB; test product applied to one axilla and control product applied to other axilla). The increase in thermal efficacy of each product versus the control is shown in the following table. In addition, the table also notes any unacceptable aesthetic attributes.

TABLE

| | Comp. 1 | Comp. 2 | Ex. 1 | Ex. 2 |
|---|---|---|---|---|
| Efficacy (absolute sweat reduction % pts. over std. gel) | +11 pts | +7 pts | +11 pts | +16 pts |
| Negative Aesthetics | White Clumps | White Clumps | None | None |

From the above data, it will be seen that the compositions of the present invention, namely examples 1 and 2, did not have the negative aesthetic attributes of the comparative examples, Comp.1 and Comp.2. In addition, although example 1 contained less antiperspirant active than the comparative examples (17% USP vs. 18% USP), it nonetheless achieved the same (Ex. 1 vs. Comp.1) or better efficacy (Ex. 1 vs. Comp.2). The composition of Ex. 2 had substantially better efficacy than all of the other examples.

What is claimed is:

1. An antiperspirant composition comprising a water-in-silicone oil emulsion that includes a water phase and a silicone oil phase, wherein the water phase includes an antiperspirant salt dissolved therein, said antiperspirant salt comprising a calcium enhanced aluminum-zirconium chlorohydrate, and wherein the silicone oil phase includes, by weight of the emulsion, less than about 5% of a non-volatile oil and about 2% to about 25% of a volatile linear silicone.

2. The antiperspirant composition of claim 1 wherein the water phase comprises about 65% to about 95% by weight of the emulsion and the silicone oil phase comprises about 5% to about 35% by weight of the emulsion, and wherein the water phase includes about 8% to about 30% by weight of the emulsion of the antiperspirant salt dissolved therein.

3. The antiperspirant composition of claim 1 wherein the water phase comprises about 70% to about 90% by weight of the emulsion and the silicone oil phase comprises about 10% to about 30% by weight of the emulsion, and wherein the water phase includes about 10% to about 28% by weight of the emulsion of the antiperspirant salt dissolved therein.

4. The antiperspirant composition of claim 1 or 2 wherein the silicone oil phase includes, by weight of the emulsion, about 0% to about 3% of the non-volatile oil.

5. The antiperspirant composition of claim 4 wherein the silicone oil phase includes, by weight of the emulsion, about 5% to about 15% of the volatile linear silicone.

6. The antiperspirant composition of claim 5 wherein the non-volatile oil is a non-volatile silicone oil.

7. The antiperspirant composition of claim 3 wherein the silicone oil phase includes, by weight of the emulsion, 0% to about 3% of the non-volatile oil and about 5% to about 15% of the volatile linear silicone.

8. The antiperspirant composition of claim 7 wherein the non-volatile oil is a non-volatile silicone oil.

9. The antiperspirant composition of claim 1, 2 or 7 wherein the volatile linear silicone comprises at least one silicone having the formula $(CH_3)_3SiO\{(CH_3)_2SiO\}_xSi(CH_3)_3$, wherein x is 0–7.

10. The antiperspirant composition of claim 1, 2 or 7 wherein the volatile linear silicone comprises at least one silicone having the formula $(CH_3)_3SiO\{(CH_3)_2SiO\}_xSi(CH_3)_3$, wherein x is 0–5.

11. The antiperspirant composition of claim 1, 2 or 7 wherein the volatile linear silicone has a viscosity of about 0.6 to about 3.0 cst ($mm^2/s$).

12. The antiperspirant composition of claim 1, 2 or 7 wherein the volatile linear silicone has a viscosity of about 1.0 to about 2.0 cst ($mm^2/s$).

13. The antiperspirant composition of claim 1 wherein the composition has a clarity better than 100 NTU at 21° C.

14. The antiperspirant composition of claim 13 wherein the composition is in the form of a gel.

15. The antiperspirant composition of claim 14 wherein the gel has a viscosity of about 50 Pas to about 200 Pas at 21° C.

16. The antiperspirant composition of claim 1, 2 or 7 wherein the silicone oil phase comprises a volatile cyclic silicone and a silicone copolyol surfactant.

17. The antiperspirant composition of claim 16 wherein the water phase additionally comprises a lower alkanol and/or a polyhydric alcohol.

18. The composition of claim 17 wherein the lower alkanol is ethanol and the polyhydric alcohol is propylene glycol.

* * * * *